(12) United States Patent
Lopes

(10) Patent No.: US 9,365,869 B2
(45) Date of Patent: Jun. 14, 2016

(54) PROCESS FOR PRODUCING ALCOHOL BY FERMENTATION OF SUGARS

(71) Applicant: Advel Technologia E Comércia Ltda., Sumaré (BR)

(72) Inventor: José Francisco Lopes, Sumare (BR)

(73) Assignee: ADVEL TECNOLOGIA E COMERCIA LTDA. (BR)

( * ) Notice: Subject to any disclaimer, the term of this patent is extended or adjusted under 35 U.S.C. 154(b) by 0 days.

(21) Appl. No.: 14/417,133

(22) PCT Filed: Jul. 24, 2013

(86) PCT No.: PCT/BR2013/000267
§ 371 (c)(1),
(2) Date: Jan. 23, 2015

(87) PCT Pub. No.: WO2014/015405
PCT Pub. Date: Jan. 30, 2014

(65) Prior Publication Data
US 2015/0225746 A1    Aug. 13, 2015

(51) Int. Cl.
*C12N 13/00* (2006.01)
*C12P 7/06* (2006.01)
*C12M 1/00* (2006.01)
*C12M 1/42* (2006.01)

(52) U.S. Cl.
CPC ........ *C12P 7/06* (2013.01); *C12M 21/12* (2013.01); *C12M 35/02* (2013.01); *C12N 13/00* (2013.01); *Y02E 50/17* (2013.01)

(58) Field of Classification Search
None
See application file for complete search history.

(56) References Cited

U.S. PATENT DOCUMENTS

| 4,451,566 A | 5/1984 | Spencer |
| 4,885,247 A * | 12/1989 | Datta ............................ 435/139 |
| 8,062,872 B2 * | 11/2011 | Kelley et al. .................. 435/165 |

FOREIGN PATENT DOCUMENTS

| EP | 0041373 A1 | 12/1981 |
| WO | WO-2007/064545 A2 | 6/2007 |
| WO | WO-2008/024331 A2 | 2/2008 |

OTHER PUBLICATIONS

Nakanishi et al., Effect of Electric Current on Growth and Alcohol Production by Yeast Cells, Journal of Fermentation and Bioengineering, vol. 85, No. 2, 250-253, 1998.*
English abstract for JP2011-223988.
Kotoyoshi Nakanishi et al. Effect of electric current on growth and 1 a 13 alcohol production by yeast cells. Journal of Fermentation and Bioengineering. 85(2): 250.
Nakanishi, Kotoyoshi, Effect of Electric Current on Growth and Alcohol Production by Yeast Cells, Journal of Fermentation and Bioengineering, vol. 85, No. 2, 250-253, 1998.

* cited by examiner

*Primary Examiner* — Suzanne M Noakes
*Assistant Examiner* — Stephen Chong
(74) *Attorney, Agent, or Firm* — Fishman Stewart PLLC

(57) ABSTRACT

A process for increasing a production of alcohol by fermenting sugars may include applying a direct current electrical field to a fermentation broth, which occurs before the fermentation broth inoculates with a concentration of yeasts; and controlling a pH value of said fermentation broth to maintain the pH value with a specific range.

20 Claims, No Drawings

PROCESS FOR PRODUCING ALCOHOL BY FERMENTATION OF SUGARS

CROSS-REFERENCE TO RELATED APPLICATIONS

This application claims priority to Brazilian Patent Application No. 1120120185756, filed Jul. 26, 2012, and International Patent Application No. PCT/BR2013/000267, filed Jul. 24, 2013, both of which are hereby incorporated by reference in their entirety.

TECHNICAL FIELD

This invention relates to a physical chemical process for improving the production of alcohol through the fermentation of sugars which includes establishing polarisation in the fermentation broth by means of an electrical field.

BACKGROUND

Alcohols are a class of chemical compounds characterized in that they contain at least one hydroxyl group (OH) and they are extensively used in industry. The best known compound in this class is ethanol or ethyl alcohol. This can be found in alcoholic drinks, cleaning products and pharmaceutical products and it is extensively used as a chemical solvent; it also has an application as a fuel for motor vehicles, which is currently its highest value and most intense use.

The process for producing ethanol is generally carried out on sugar cane, but it may also be carried out on a variety of grains and sources of sugar such as maize, cassava, other roots, sorghum, wheat, barley and molasses, syrup, cane bagasse, potatoes, whey, etc.

The manufacture of ethanol is basically divided into 4 stages: milling, liquefaction, fermentation and distillation. Milling comprises passage from the source of sugar by a processor. In this stage there is obtained a broth which contains a high concentration of water and sugars.

The fermentation part comprises the addition of some kind of yeast which causes the sugar present in the solution to be converted into ethanol. It is the action of enzymes which carries out this work. After this process a fermented must is obtained, and this already contains part of its total volume converted into ethanol.

The must then continues on to the last stage, fractional distillation, and will give rise to a solution having the composition of ethanol and water.

The stage most directly affecting the result of ethanol production, and therefore the most studied, is fermentation, also known as alcoholic fermentation, which is the chemical process of converting sugars, mainly saccharose, glucose and fructose, into ethanol. Microbiological agents which are responsible for the conversion of sugars into ethanol take part in this process.

As it is a widely known process in the state of the art various documents describing processes for the purpose described above can be found. In general the processes concentrate on finding an ideal species or combination of species for the production of ethanol, given that the process used involves a significant loss of the raw materials (sugars), thus reducing the efficiency of the process.

Various documents dealing with different processes for the production of ethanol can be found in the patent literature. American patent U.S. Pat. No. 4,451,566 by Donald B. Spencer describes methods and equipment for the enzyme production of ethanol from fermentable sugars. A sequence of enzymes for catalysing conversion of the sugars into ethanol is maintained in a variety of reaction zones. The fermentable sugar solution passes through these zones in sequence and alcohol is recovered in the last zone. Apart from providing a more efficient reaction than the usual process, this document provides a solution which is onerous, complex and difficult to maintain.

International patent application WO 2007/064545 by Brian Burmaster describes a process for improving the yield of ethanol, reducing the fermentation time and reducing the formation of by-product by monitoring and controlling the oxidation-reduction potential of the fermenter. However this process requires very specific monitoring and is difficult to maintain, causing the process to be expensive, even though it is more efficient.

International patent application WO 2008/024331 by Vladimir Vlad describes a method for magnetic fermentation which includes subjecting a biological material to a static magnetic field in order to affect fermentation of the biological material into a fermented product. The fermentation reaction can take place in alkaline or acid medium and the magnetic field may be positive or negative. This document makes use of a static magnetic field to provide a more propitious environment for the cellular reproduction of microorganisms. Apart from increasing the number of microorganisms in the alcoholic fermentation and thus increasing the reaction yield, this process requires constant monitoring and total control of the reaction, which renders the process expensive.

Noting the limitations of the state of the art the inventor has developed a process for the production of alcohol through the fermentation of sugars which brings benefits such as an increase in the efficiency of the process, through continuous electrical polarisation during the fermentation.

SUMMARY

Processes for the production of alcohol through the fermentation of sugars are already known to those skilled in the art. However all the processes used for the production of alcohol through alcoholic fermentation either have substantial shortcomings in the yield from the fermentation reaction, giving rise to losses of raw material (sugars), or require equipment or a process with a high cost of implementation or maintenance. Thus the object of this invention is to provide an improved low-cost physical chemical process for the production of alcohol through the fermentation of sugars which offers a high level of utilization of the raw material (sugars) and their by-products, consequently increasing the yield of the fermentation reaction.

Fermentation processes are already well established, and involve a great cost of materials. Thus one object of the invention is to provide a process which can be easily implemented in already installed facilities, providing better efficiency in the sugar fermentation process.

DETAILED DESCRIPTION

This invention provides a physical chemical process for increasing and improving the yield of alcohol production through modifications and improvements in the stage of the fermentation of sugar-containing solutions. This improvement comprises applying a direct current electrical field, causing dynamic polarisation of the sugars, together with electrolysis of the must, which in fact originates from the water present in the must which is almost wholly acidified.

The application of an electrical field to the processed broth (sugar-containing solution) has the result that polarisation is brought about in the molecules of the sugars present in the processed broth. The formation of these electrical polarisations increases the selectivity of the sugar molecules, thus increasing the process yield.

In order that this selectivity can take place with the desired efficiency the fermentation process must only begin after the electrical field has been applied to the processed broth. Once all the molecules are electrically orientated the fermentation can begin.

The electrodes described in this invention are devices made of conducting metal.

The process described in this invention comprises the following steps:
1. Preparing a container for the processed broth containing at least 2 electrodes;
2. Connecting the electrodes to a source of direct current;
3. Preparing the broth for fermentation;
4. Filling the container batchwise or continuously;
5. Connecting the electrodes to orientate the sugar molecules; and
6. Starting the fermentation process.

In one aspect of this invention the equipment includes means for controlling and maintaining fermentation parameters such as voltage and current.

A number of tests were performed to evaluate the efficacy applying the electrical field to the fermentation broth. One example of a process which is not intended to restrict the scope of protection of the invention follows below.

Example of a Process for the Production of Ethanol Through the Fermentation of Sugars.

The process described below not only includes the application of an electrical field to the prepared broth, but all the stages for the production of ethanol from sugar cane.

We will consider a present-day case of a modern factory which has 12 (twelve) vats each of 300,000 liters, where this volume comprises cane broth, steeping water plus the sum of chemical products, these products amounting on average to $6 \times 10^{-4}$ kg/l or 180 kg per vat of 300,000 liters.

Through fermentation and distillation this factory produces 9 to 10% of ethanol from the 300,000 liters in each vat, that is 27,000 to 30,000 liters of ethanol per batch in each vat.

A direct current electrical field is introduced into each vat bringing about dynamic polarisation of the saccharose, together with electrolysis of the must, which in fact originates from water which is almost wholly acidified. Two types of gases are naturally formed in this type of fermentation combined with electrolysis:
the fermentation gas, which is bubbles of carbon dioxide gas,
the electrolysis gas, where basically the gases in acid medium are ionic in water with a small contribution from other gases relating to chemical elements present in the must in a very low concentration.

This means that there will be an increase in the volume of gases in the fermentation vats. Dynamic polarisation of the sugars plus the increase in volume of the gases and their reactivities will also give rise to a volume of ETHANOL and other compounds, in addition to those from simple alcoholic fermentation.

For the purposes of illustrating this invention the term TRS will be used to mean "total reducing sugars". We will also use the term BRIX to mean the hydrometric scale for measuring the concentration of sugars in a particular solution at a particular temperature. These terms are already well established in the state of the art and will be readily understood by a person skilled in the art.

The pH in the vat at the start of fermentation is approximately 4.5. The BRIX for the must when fermenting varies from 18 to 22 with an alcohol content of approximately 8%. When the fermentation starts the total reducing sugars, TRS, together with the BRIX are on a decreasing scale, their concentrations falling, and the pH of the must which is becoming acidic decreases to 3.5 as the temperature rises. The temperature of the must should not rise, because this will cause the growth of microorganisms which will consume some of the TRS still remaining in the process.

Anodes and Cathodes

The anodes and cathodes are geometrically identical. They comprise coils with a sheet between the turns, approximately equal to the diameter of the tubes, which should be of copper of 99.9% purity. These are made to the dimensions of the existing vats, which now already reach 10 (ten) meters in diameter and each have a capacity of 1000 m³ of must.

The functions of the tubular-shaped ANODES and CATHODES comprise:
conducting the cathodic and anodic direct current;
bringing about cooling of the must through a flow of demineralized and deionised water in a closed circuit, holding the temperature of the must below or equal to 35° C., using the water passing through the cathode and anode coils.

The shape of the spirals depends on the shape of the vat, and they are present in pairs, and there must at least be one pair. These spirals are supported on insulating material supports which do not allow electrical contact between them and the sides of the vats. The current circulating in these spirals may be switched in polarity in order to prevent the deposition of anodic sludge on the anodes. The distance between the anode and the cathode will depend on the amperage and voltage, varying automatically in accordance with the changes in pH.

As the pH of the must becomes acidic, an automatic injection of a broth of lime or other alkalies is injected.

Process Gases

The fermentation gas is $CO_2$ (or carbon dioxide gas) which decreases with the fermentation process. When no more $CO_2$ forms it means that almost all the sugars have been converted and all the must has to proceed to distillation. The reactive gases are ionic, capable of reacting in the formation of ethanol and other products. They take different forms and themselves maintain a pH around 4.5 and a temperature below 35° C., remaining approximately constant throughout all the fermentation process even after $CO_2$ formation ceases with the natural end of fermentation. Thus part of the alcohol is also continuously drawn off in the form of vapor. These alcohol vapors should preferably be condensed and recovered without passing through distillation of the final must. This will also allow capture of almost all the $CO_2$, which is now discharged to the atmosphere. In this way the atmospheric emission of $CO_2$, which is of the order of 1 cubic meter for each cubic meter of ethanol, will be substantially reduced.

Dynamic Polarization of Saccharose

As the saccharose molecules are dynamically polarized they will always be orientated, aiding their conversion.

Automation of the Process

In automating the process pH must be controlled to the most appropriate level for each stage in the fermentation. This control will be implemented through the pumps metering the lime broth or equivalent, because the trend during the course of the process is to further acidify the remaining fermenting must. Because of the change in pH during the fermentation process there will be changes in the density of the electrical current, which will also have a system for measuring and controlling this, mainly in the batch process.

Those skilled in the art will understand that the process described in this invention is not restricted to the specific features of the process of ethanol fermentation, and this process can be extended to each and every fermentation process known in the state of the art, providing efficiency and speed and an increase in the production of alcohol.

The invention claimed is:

1. A process for increasing a production of alcohol by fermenting sugars, comprising: applying a direct current electrical field to a fermentation broth, which occurs before the fermentation broth inoculates with a concentration of yeasts, and controlling a pH value of said fermentation broth to maintain the pH value within a specific range.

2. The process as claimed in claim 1, wherein controlling the pH value of said fermentation broth further includes continuing to maintain the pH value within a pH range of 6 to 4.5 while applying the direct current electrical field to said fermentation broth.

3. The process as claimed in claim 1, further comprising maintaining a temperature of said fermentation broth within a range from 30° C. to 35° C. while applying the direct current electrical field to said fermentation broth.

4. The process as claimed in claim 1, wherein said pH value of the fermentation broth is maintained at approximately 4.5.

5. The process as claimed in claim 3, wherein maintaining the temperature of said fermentation broth further includes continuously controlling the fermentation broth at a pH of approximately 4.5 and a temperature between 30° and 35° C. until completion.

6. The process as claimed in claim 1, wherein controlling the pH value of the fermentation broth includes a control system with a pump, and injecting a basic material into the fermentation broth and measuring the pH value.

7. The process as claimed in claim 1, wherein prior to applying the direct current electrical field to the fermentation broth, further comprising the following steps:
   (i) preparing a container for receiving the fermented broth and positioning at least two electrodes in the container;
   (ii) connecting the electrodes to a source of direct current;
   (iii) preparing the fermentation broth; and
   (iv) filling the container with the fermentation broth at least one of in batches and continuously.

8. The process as claimed in claim 7, wherein, after the step of filling the container with the fermentation broth, the step of applying the direct current electrical field to the fermentation broth is performed to polarize said sugars, and subsequently further including the step of adding the concentration of yeasts to the fermentation broth to initiate fermentation.

9. The process as claimed in claim 7, wherein preparing the fermentation broth includes adding a concentration of sugar to water, and wherein the concentration of sugar includes at least one of a saccharose, a fructose and a glucose.

10. The process as claimed in claim 1, wherein applying the direct current electrical field to the fermentation broth further includes polarizing a concentration of a plurality of sugar molecules to orient said plurality of sugar molecules.

11. The process as claimed in claim 1, wherein controlling the pH value of said fermentation broth includes injecting a concentration of at least one alkali into the fermentation broth in response to exceeding the specific range of the pH value.

12. The process as claimed in claim 1, wherein applying the direct current electrical field to the fermentation broth occurs via at least two electrodes.

13. The process as claimed in claim 12, further comprising maintaining a constant potential difference between the at least two electrodes.

14. The process as claimed in claim 1, wherein applying the direct current electrical field to the fermentation broth further includes monitoring at least one of an amperage and a voltage of the electrical field and adjusting, via at least one of a voltage variator and a current variator, the at least one of the amperage and the voltage in response to a change in the pH value.

15. The process as claimed in claim 1, further comprising recovering the fermented product.

16. The process as claimed in claim 2, further comprising maintaining a temperature of said fermentation broth within a range of 30° C. and 35° C. while applying the direct current electrical field to said fermentation broth.

17. The process as claimed in claim 2, wherein said pH value of the fermented broth is maintained at approximately 4.5.

18. The process as claimed in claim 2, further comprising injecting a lime broth into the fermentation broth in response to exceeding the pH range of 6 to 4.5.

19. The process as claimed in claim 3, wherein maintaining the temperature of said fermentation broth includes circulating a flow of at least one of a demineralized water and a deionised water in a closed circuit through the fermentation broth.

20. A process for increasing a yield of alcohol from fermentable sugars, comprising:
   preparing a fermentation broth composed of a high concentration of a plurality of water molecules and a plurality of sugar molecules;
   positioning at least two electrodes in the fermentation broth;
   applying a direct current electrical field to the fermentation broth via the at least two electrodes until a specified amount of the plurality of the sugar molecules are polarized;
   inoculating a concentration of yeasts into the fermentation broth after the specified amount of the plurality of sugar molecules are polarized;
   controlling a pH value of the fermentation broth to preserve a pH range of 6 to 4.5;
   maintaining a temperature of the fermentation broth between 30° C. to 35° C.; and
   recovering the fermented product;
   wherein applying the direct current electrical field to the fermentation broth is maintained continuously until the recovery of the fermented product.

* * * * *